(12) United States Patent  (10) Patent No.: US 8,379,795 B2
Mabini et al.  (45) Date of Patent: Feb. 19, 2013

(54) METHODS AND APPARATUS FOR ARCHIVING X-RAY FLUOROSCOPY IMAGES

(75) Inventors: Daniel Mabini, Waukesha, WI (US); John Close, Brookfield, WI (US); Rathinasabapathy Ramalingam, Bangalore (IN); Base Varghese Paul, Waukesha, WI (US); Jon Charles Omernick, Wauwatosa, WI (US); Ellyn Mae Schulte, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 257 days.

(21) Appl. No.: 12/847,878

(22) Filed: Jul. 30, 2010

(65) Prior Publication Data

US 2012/0027178 A1  Feb. 2, 2012

(51) Int. Cl.
 *H05G 1/64* (2006.01)
(52) U.S. Cl. .......................................... 378/98
(58) Field of Classification Search .................... 378/98, 378/98.2, 98.5, 62
See application file for complete search history.

(56) References Cited

U.S. PATENT DOCUMENTS

| 4,924,487 | A | * | 5/1990 | Nishiki ........................ 378/190 |
| 5,917,882 | A | | 6/1999 | Khutoryansky et al. |
| 6,031,888 | A | | 2/2000 | Ivan et al. |
| 6,298,112 | B1 | | 10/2001 | Acharya et al. |
| 7,543,239 | B2 | | 6/2009 | Viswanathan et al. |

* cited by examiner

*Primary Examiner* — Jurie Yun
(74) *Attorney, Agent, or Firm* — The Small Patent Law Group; Dean D. Small

(57) ABSTRACT

Methods and apparatus for archiving x-ray fluoroscopy images are provided. One method includes receiving fluoroscopic images from a fluoroscopic imaging system and storing all of the received fluoroscopic images during an image acquisition scan by the fluoroscopic imaging system. The received fluoroscopic images are displayed during the image acquisition scan.

21 Claims, 6 Drawing Sheets

METHODS AND APPARATUS FOR ARCHIVING X-RAY FLUOROSCOPY IMAGES

BACKGROUND OF THE INVENTION

The subject matter disclosed herein relates generally to diagnostic imaging systems, and more particularly to x-ray fluoroscopy imaging systems.

Diagnostic imaging systems are used in many different applications and can provide anatomical and/or physiological information for a patient. One type of diagnostic imaging system is an x-ray fluoroscopy system that acquires real-time moving images of the internal structures of a patient using a fluoroscope. Fluoroscopy has many uses in diagnostic and image-guided procedures, including general-purpose fluoroscopy, vascular imaging, etc.

In conventional fluoroscopy systems, different modes of operation are typically provided including a mode for viewing images in real-time (often referred to as a fluoro mode) and another mode for capturing images at the point (spatial/temporal) of interest for storing and later analysis (often referred to as a digi-record or digital record mode). Thus, radiologists must use the fluoro mode to observe evidence of pathology, and then initiate digital record exposures to subsequently record the images. An alternative process is for the radiologist to observe a patient during fluoro mode and immediately stop exposure and save the last image of the sequence. An additional alternative process for the radiologist is to use the fluoro mode to observe the image sequence, then start a fluoro sequence save to store the sequence once completed.

In fluoroscopic exams with fast moving anatomy, the time to switch modes and begin recording of images to record the pathology of interest is very fast and may be less than one or two seconds. Accordingly, initiating a digital record is difficult for these procedures, such as swallow or speech pathology studies, where the contrast material is moving quickly. The transition from the fluoro mode to the record mode typically requires approximately two seconds. Thus, the radiologist often must repeat the procedure (including multiple swallows of barium) and take numerous exposures to time the acquisition properly, thereby adding time to the overall scan and increasing patient dose. When using the last image hold save, user timing to stop the sequence at the proper moment is again required.

Thus, saving of a fluoro sequence often requires the radiologist to repeat the procedure twice at a minimum at a minimum, once to observe, and then a second time to record the pathology of interest. This sequence is generally limited to 10-20 seconds with the initial data deleted once a storage maximum is reached, such that a user must time the fluoro sequence carefully to avoid losing data.

BRIEF DESCRIPTION OF THE INVENTION

In accordance with one embodiment, a method for archiving x-ray fluoroscopic images is provided. The method includes receiving fluoroscopic images from a fluoroscopic imaging system and storing all of the received fluoroscopic images during an image acquisition scan by the fluoroscopic imaging system. The received fluoroscopic images are displayed during the image acquisition scan.

In accordance with another embodiment, a method for archiving x-ray fluoroscopic images is provided. The method includes storing on a persistent basis all of a plurality of fluoroscopic image sequences acquired during an imaging scan using a fluoroscopic imaging system. The fluoroscopic image sequences are stored directly to a memory storage device of the fluoroscopic imaging system. The method further includes storing on a permanent basis at least some of the plurality of fluoroscopic image sequences previously stored on a persistent basis.

In accordance with yet another embodiment, an x-ray fluoroscopy imaging system is provided that includes an x-ray generator configured to generate and emit low dose x-rays and an x-ray detector configured to detect low dose x-rays emitted from the x-ray generator after passing through an object to generate low dose x-ray fluoroscopy data. The x-ray fluoroscopy imaging system further includes a memory configured to store the low dose x-ray fluoroscopy data from the x-ray detector on a persistent basis during acquisition of the low dose x-ray fluoroscopy data. The x-ray fluoroscopy imaging system also includes a display configured to display fluoroscopic images generated from the low dose x-ray fluoroscopy data, wherein the fluoroscopic images are displayed during acquisition of the low dose x-ray fluoroscopy data.

DETAILED DESCRIPTION OF THE INVENTION

Figure 1:
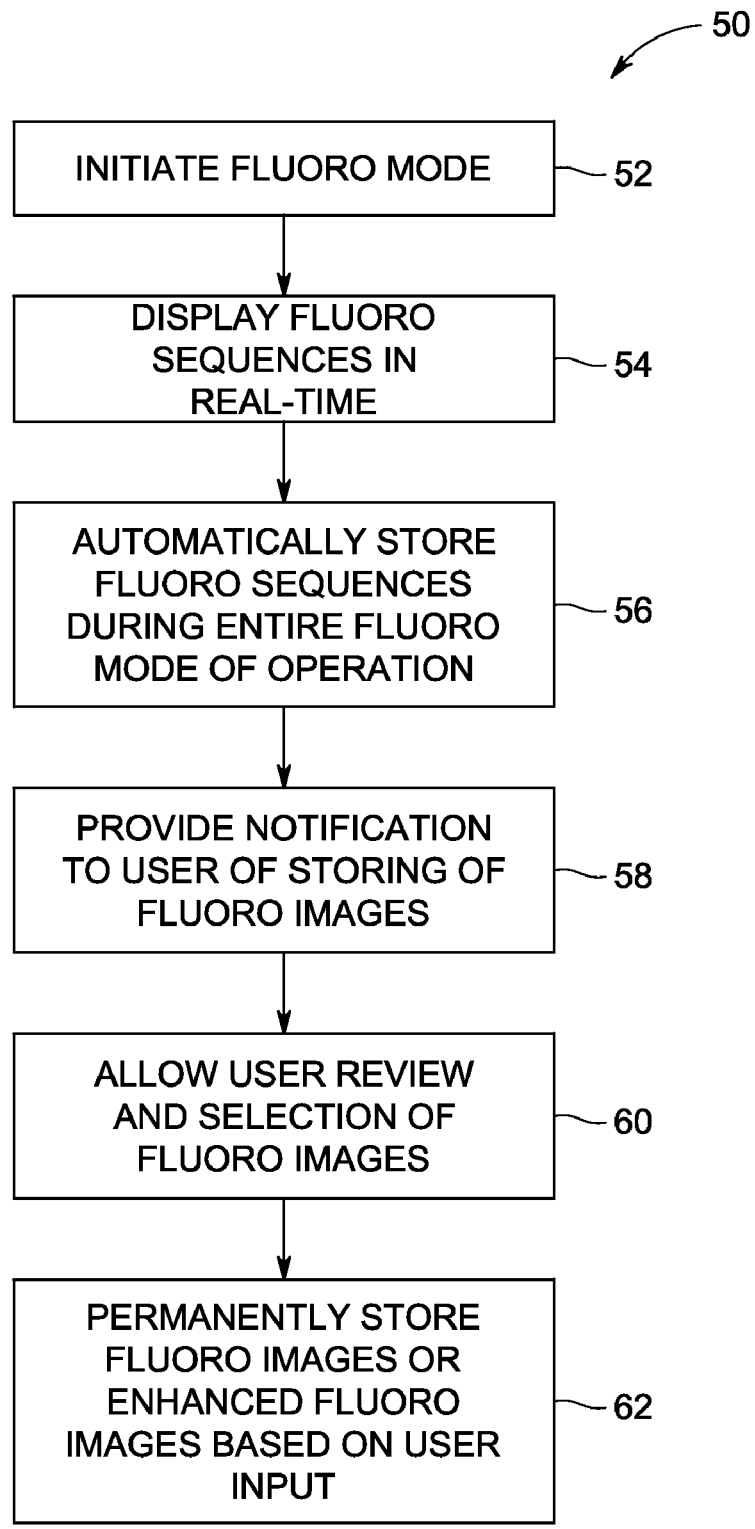
FIG. 1 is a flowchart of method for archiving fluoroscopic data in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide methods and systems for archiving image data during an x-ray fluoroscopic exam. In particular, fluoroscopy or fluoroscopic images (also referred to herein as fluoro images) are saved on a persistent basis during real-time viewing of fluoro image sequences. The various embodiments allow a user after viewing a fluoro sequence, to select for review and permanent storage an entire sequence, partial sequences or enhanced single images. By practicing various embodiments and at least one technical effect of the various embodiments is a reduced number of imaging sequences with a corresponding reduced exam time and dose to the patient.

Although the various embodiments are described in connection with an x-ray fluoroscopic imaging system, the systems and methods described herein may be used with different types of medical (e.g., magnetic resonance imaging, ultrasound imaging, computed-tomography imaging, etc.) and non-medical (e.g., non-destructive testing systems, such as airport screening) imaging systems.

In accordance with various embodiments, a method 50 as illustrated in FIG. 1 for archiving x-ray data, and in particular fluoroscopic images acquired by an x-ray fluoroscopic imaging system. It should be noted that although the steps of the method 50 are illustrated in a sequential manner, the order of the steps may be changed or modified. Additionally, two or more of the steps (or portions thereof) may be performed simultaneously or concurrently.

The method 50 provides a persistent storing of acquired fluoro images and sequences. In particular, the method 50 includes initiating a fluoro mode of operation of the fluoroscopic imaging system at 52, which may be initiated by a user input. The initiation of the fluoro mode starts the acquisition of a plurality of fluoro images or frames by the fluoroscopic imaging system, which may define an acquisition mode or scan. The images or frames acquired in the fluoro mode are acquired using low dose x-ray scanning techniques as described in more detail below.

The images or frames being acquired are also displayed in real-time at 54. For example, real-time fluoro sequences or image loops are displayed to a user while the fluoroscopic imaging system is in the fluoro acquisition mode. The real-time fluoro sequences or image loops may be displayed on one of a plurality of display monitors or on a portion of a display monitor. In some embodiments, real-time fluoro sequences or image loops are displayed in an image acquisition portion of the display monitor. It should be noted that in addition to the real-time fluoro sequences or image loops, a last image of the sequence (often referred to as a last image hold (LIH) is also displayed. In some embodiments, a plurality of fluoro sequences and LIHs are displayed sequentially on the display monitor. For example, a thumbnail type view of the real-time fluoro sequences or image loops for the current exam may be displayed. It should be noted that when used herein, real-time generally refers to displaying images while the system is acquiring images (e.g., x-ray exposures are active).

The fluoro sequences or image loops are automatically stored at 56, which includes storing all of the fluoro sequences or image loops that are or were displayed in real-time to a user, such as for a particular or current scan. Thus, the fluoro sequences or image loops are stored from the time when the fluoro mode is initiated and continues during the entire fluoro mode of operation, for example, throughout and entire scan from start to finish. Accordingly, all the fluoro sequences or image loops acquired during the fluoro mode are stored automatically on a persistent basis. It should be noted that a user does not have to select or initiate a record function or operation (e.g., digi-record mode) to start the recording of the fluoro sequences or image loops. In some embodiments, the fluoro sequences or image loops are stored directly to a permanent memory or memory storage device (e.g., a hard disk drive) of the fluoroscopic imaging system. The fluoro sequences or image loops may be stored until otherwise deleted or modified by a user. Optionally, the fluoro sequences or image loops may be deleted after a predetermined period of time, for example, after twenty-four hours, after a predetermined number of examinations, etc. This storage of the fluoro sequences or image loops is referred to herein as a persist or persistent store. Optionally, one or more user preferences may be defined to not store fluoro sequences that are below a minimum time period. The preference(s) may be based on, for example, the user, exam type, patient type (e.g., adult or pediatric), etc.

A notification is also provided at 58 that the fluoro sequences or image loops are being stored. For example, a notification may be displayed to a user indicating that the system is storing the real-time fluoro sequences or image loops that are being displayed. In some embodiments, a sequential panel on the display monitor alerts a user that the system is storing the fluoro sequences or image loops, such as by displaying an icon or thumbnail of the sequence.

The method 50 then allows a user at 60 to review and select images, partial sequences or full sequences for further processing or for long term storage, such as a permanent store instead of a persist store. If a user selects certain images or sequences of interest, the images or sequences are stored in a permanent store memory area at 62 with the non-selected images or sequences deleted. The deletion of the non-selected images or sequences may be automatic or may require confirmation by a user. In some embodiments, the selected images or sequences also may be communicated to another system for review or analysis, such as by another radiologist. For example, the selected images or sequences may be transmitted to a Digital Imaging and Communications in Medicine (DICOM) picture archiving and communication systems (PACS) workstation located remote from the fluoroscopic imaging system.

It should be noted that selected images may be further processed, such as enhanced and thereafter stored as described above. For example, an image may be enhanced or optimized, such as performing motion correction, based on adjacent images in the image sequence. One method for enhancing the images is described in co-pending and commonly assigned application Ser. No. 12/277,088 entitled "Methods and Apparatus for Generating and Archiving X-Ray Fluoroscopy Images."

The images selected by a user also may be displayed in a review mode, which may be displayed concurrently with the acquired images on a same or different display monitor. The selected images may be, for example, annotated by a user or further processed as described above.

Figure 2:
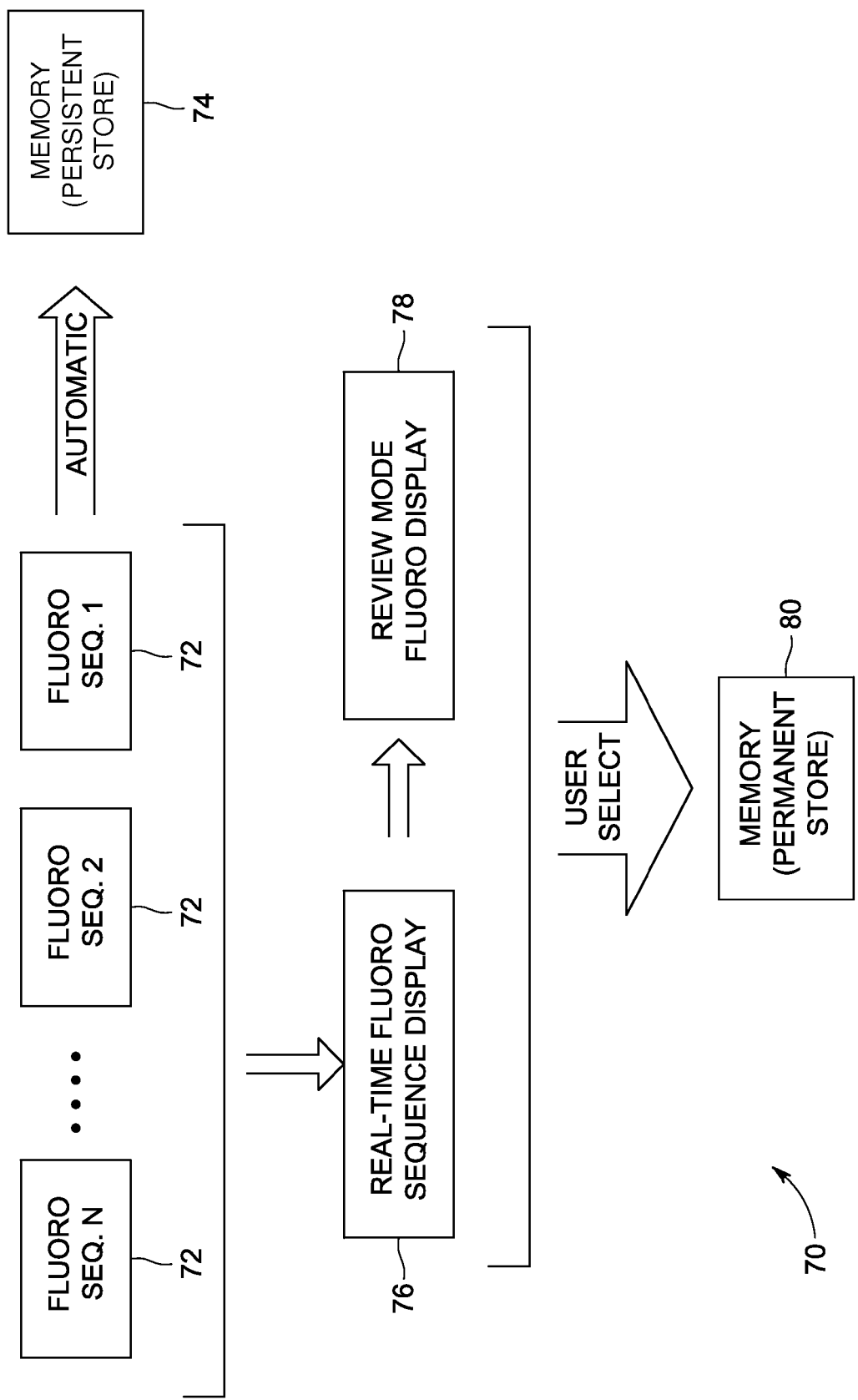
FIG. 2 is diagram illustrating a workflow for archiving fluoroscopic data in accordance with various embodiments.

In various embodiments, the persistent fluoro store may be implemented as a workflow 70 as illustrated in FIG. 2. As can be seen, a plurality of fluoro sequences 72 (or image loops) are acquired by the fluoroscopic imaging system. The fluoro sequences 72 are automatically stored without any user interaction. For example, the fluoro sequences 72 for an entire fluoroscopic image scan or session are stored directly to a system memory, such as the system hard disk drive. The fluoro sequences 72 stored during acquisition are stored in a persistent store memory 74, for example, a portion of the memory of the system hard disk drive.

During the acquisition of the fluoro sequences 72 and storing of the fluoro sequences 72 in the persistent store memory, the fluoro sequences 72 are also displayed to a user, for example, as a real-time fluoro sequence display 76, which may correspond to an acquisition portion of a display monitor. Thus, a user is able to view the fluoro sequences 72 that are being acquired and automatically stored throughout the image scan. During the acquisition or thereafter, a user is able to review the fluoro sequences 72 acquired and stored, for example, using a review mode fluoro display 78, which may correspond to a portion of the display monitor. A user is then able to determine whether images should be further processed, for example, enhanced as described in more detail herein. A user is also able to select the images or fluoro sequences 72 to be maintained in memory, which may be in a permanent store memory 80. The permanent store memory 80 may be a portion of the system hard disk drive, which may be the same portion or a different portion than the persistent store memory 74. Accordingly, the persistent stored fluoro sequences 72 selected to be maintained in memory may continue to be stored with the non-selected fluoro sequences 72 deleted from the memory of the hard disk drive.

Figure 3:
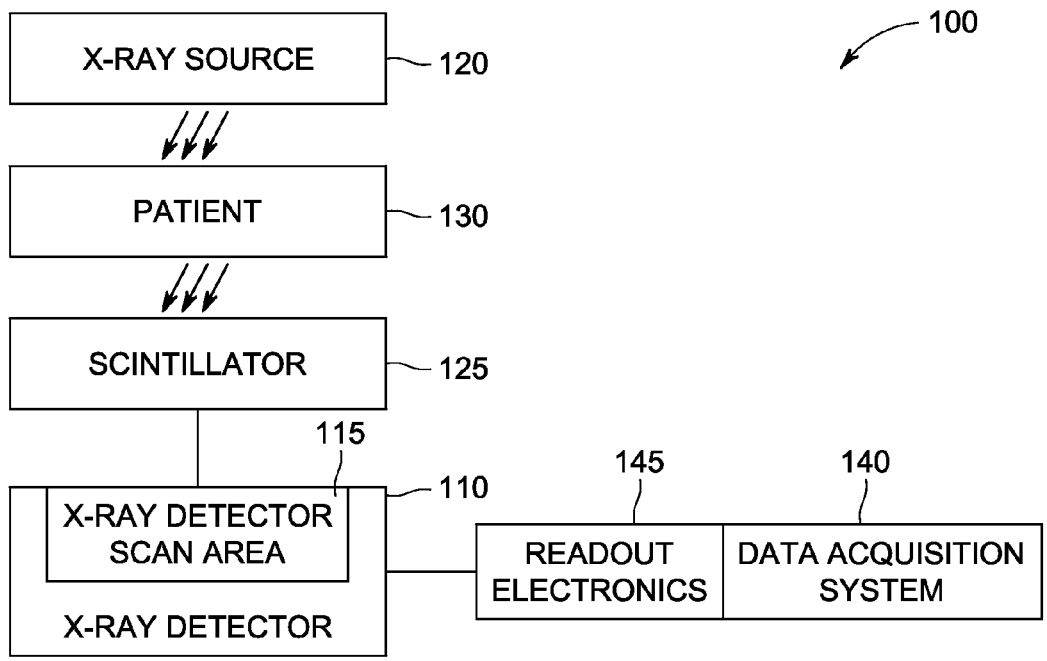
FIG. 3 is a block diagram of an imaging system formed in accordance with various embodiments.

The various embodiments of a persistent fluoro store may be implemented in different types of fluoroscopic imaging systems. For example, persistent fluoro storing may be implemented in connection with the imaging system 100 shown in FIG. 3, which is illustrated as an x-ray system that be used to perform fluoroscopic imaging as described in more detail herein in connection with FIG. 4. The imaging system 100 generally includes an x-ray detector 110 having an array 115 of detector cells, an x-ray source 120 and a scintillator 125. An object, such as a patient 130 is positioned between the x-ray source 120 and the scintillator 125. The imaging system 100 also includes a data acquisition system 140 with readout electronics 145.

In one embodiment, the scintillator 125 includes a screen positioned in front of the detector 110. Alternatively, the detector 110 may be a flat-panel detector system such as an amorphous silicon flat panel detector or other type of digital x-ray image detector.

In operation, the patient 130 is positioned in the imaging system 100 for performing an imaging scan. For example, the x-ray source 120 may be positioned above the patient 130 or below the patient 130. The x-ray source 120 also may be moved between different positions around the patient 130. The scintillator 125 is positioned between the patient 130 and the x-ray detector 110. X-rays are transmitted from the x-ray source 120 through the patient 130 to the scintillator 125. The scintillator 125 emits light in response to the x-rays transmitted from the x-ray source 120 through the patient 130. The emitted light is transmitted to the x-ray detector 110 and the x-ray detector array 115. For example, light emitted by the scintillator 125 activates or discharges photodiodes in the detector array 115 to varying degrees. The readout electronics 145 may include a reference and regulation board (RRB) or other data collection unit. The RRB may accommodate and connect data modules to transfer data from the detector 110 to the data acquisition system 140. The readout electronics 145 transmit the data from the detector 110 to the data acquisition system 140. The data acquisition system 140 forms an image from the data and may store, display, and/or transmit the image. For example, the various embodiments automatically store acquired images as described in more detail below.

Figure 4:
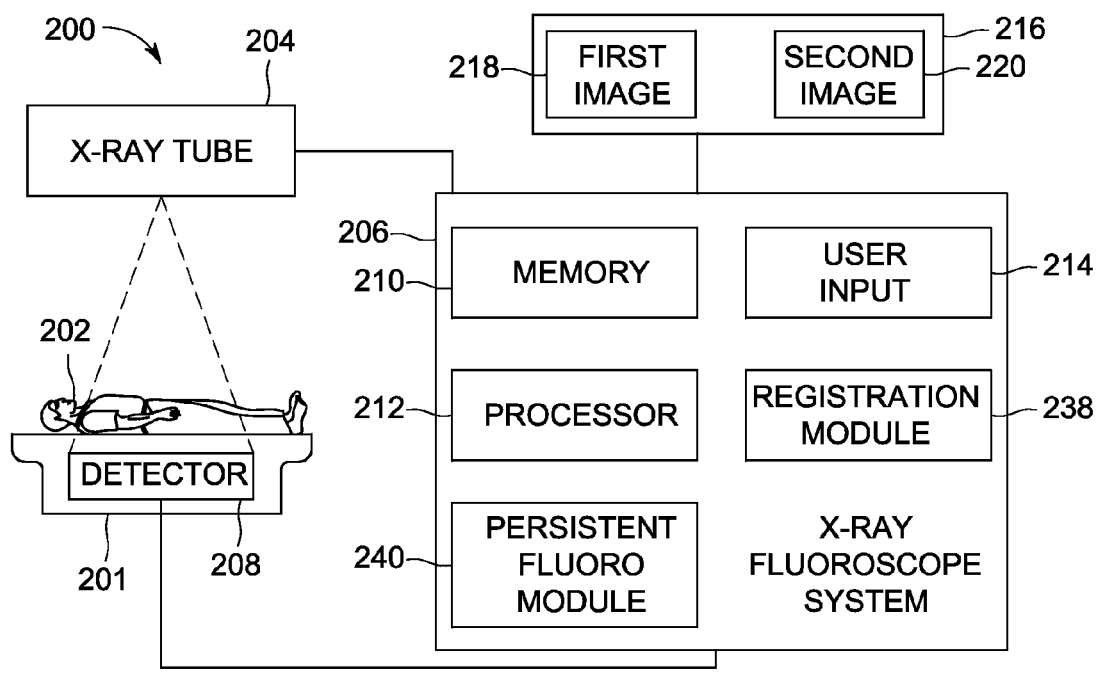
FIG. 4 is a block diagram of a fluoroscopic imaging system formed in accordance with various embodiments.

Various embodiments may be provided in connection with an x-ray fluoroscopic imaging system 200 (also referred to as a fluoroscope) as shown in FIG. 4. The x-ray fluoroscopic imaging system 200 may be used to obtain real-time moving images of the internal structures of a patient 202. The x-ray fluoroscopic imaging system 200 includes a table 201 or bed for supporting the patient 202. An X-ray tube 204 (which may form part of the system 100) or other generator is connected to an x-ray fluoroscopic processing sub-system 206. As shown, the x-ray tube 204 is positioned above the patient 202, but it should be understood that the x-ray tube 204 may be moved to other positions with respect to the patient 202. A detector 208 is positioned opposite the x-ray tube 204 with the patient 202 therebetween. The detector 208 may be any known detector capable of detecting x-ray radiation.

The x-ray fluoroscopic processing sub-system 206 includes at least a memory 210, a processor 212 and at least one user input 214, such as a keyboard, trackball, pointer, touch panel, and the like. To acquire an x-ray image, the x-ray fluoroscopic processing sub-system 206 causes the x-ray tube 204 to generate x-rays and the detector 208 detects x-rays that pass through the patient 202 and impinge on the detector 208. Fluoroscopy may be accomplished by activating the x-ray tube 204 continuously or at predetermined intervals while the detector 208 detects corresponding emitted x-rays. One or more image(s) 218 and 220, for example, fluoroscopic x-ray images generated from the detected x-rays during a low dose scan may be displayed in real-time on a display 216 that may be configured to display a single image or more than one image at the same time, such as an image sequence. It should be noted that the images 218 and 220 acquired by x-ray fluoroscopic imaging system 200 may be acquired in any known manner. The images 218 and 220 are automatically stored by in a persistent store module during image acquisition, which may be stored to an archival location. It also should be noted that the display 216 may be configured to include different portions for viewing real-time images and for reviewing and selecting images for permanent storage.

Figure 6:
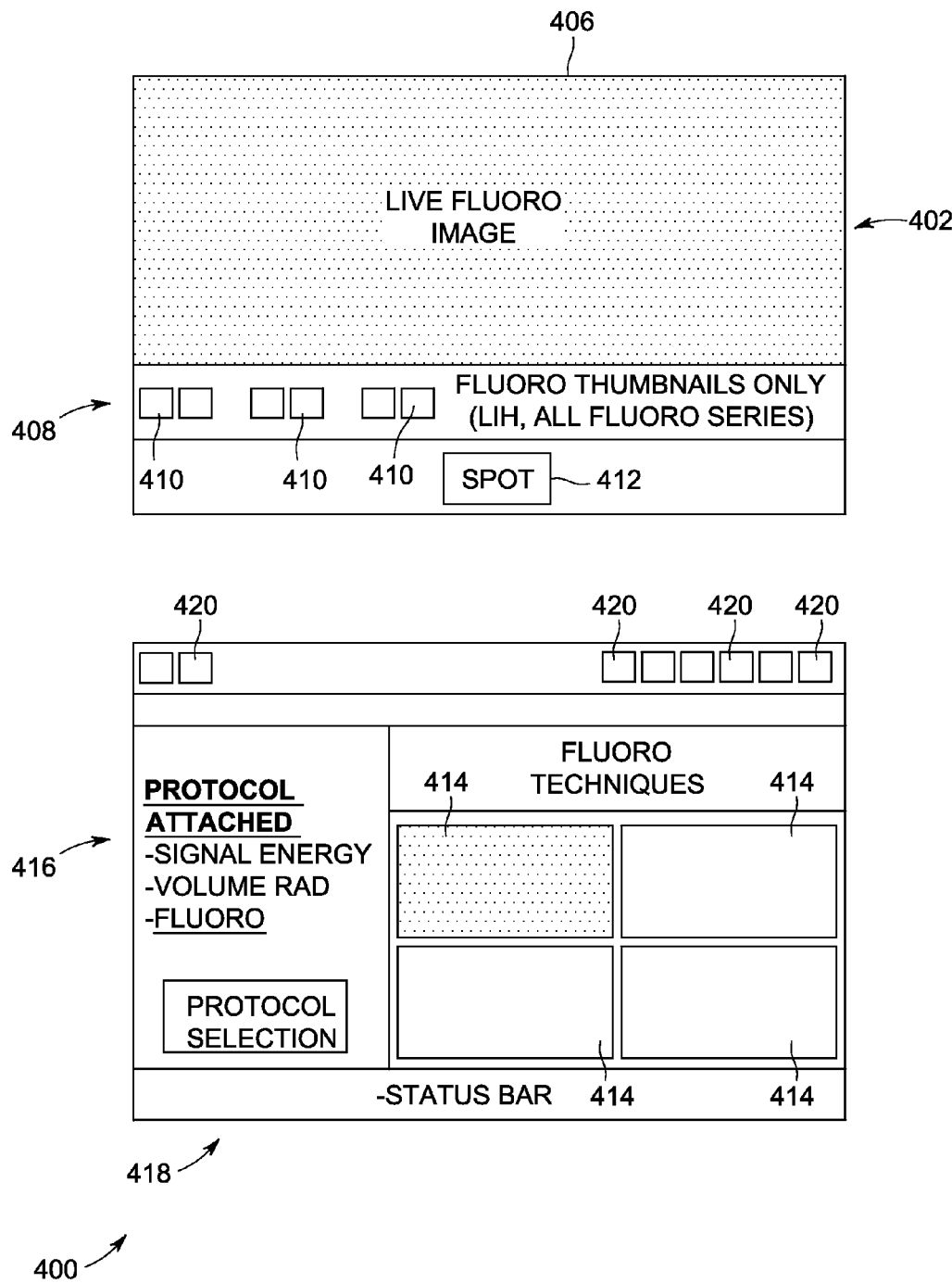
FIG. 6 is a user interface provided in accordance with various embodiments.
Figure 7:
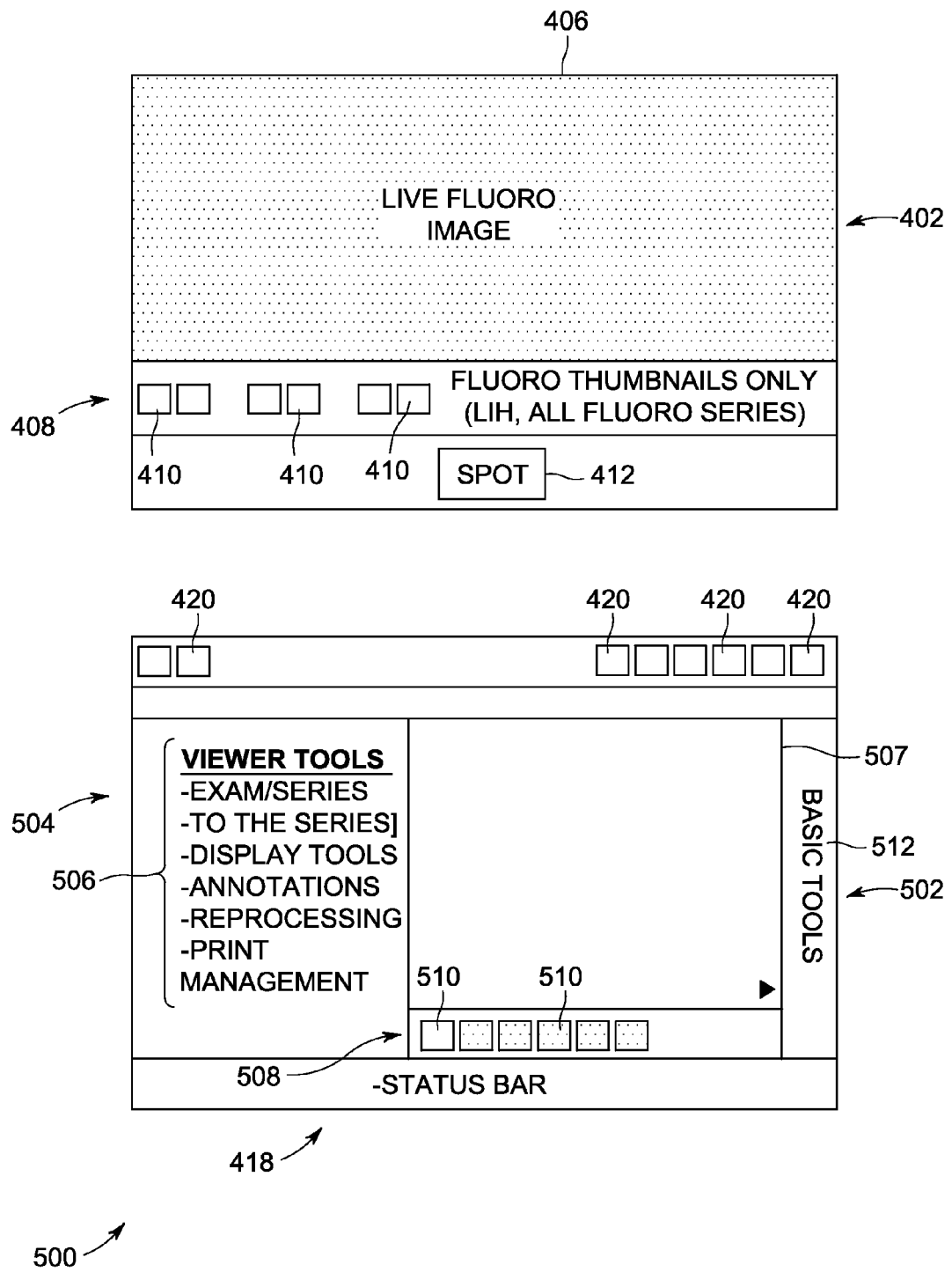
FIG. 7 is a user interface provided in accordance with other various embodiments.

The x-ray fluoroscopic processing subsystem 206 also may include a registration module 238, which may be a processor configured to process received image data to register the first and second images 218 and 220 with respect to each other. The x-ray fluoroscopic processing subsystem 206 also may include a persistent fluoro module 240 to control the real-time display of fluoro images or sequences, the automatic storing of the acquired fluoro images or sequences and the operation of a user interface as illustrated in FIGS. 6 and 7, as described in more detail below.

Figure 5:
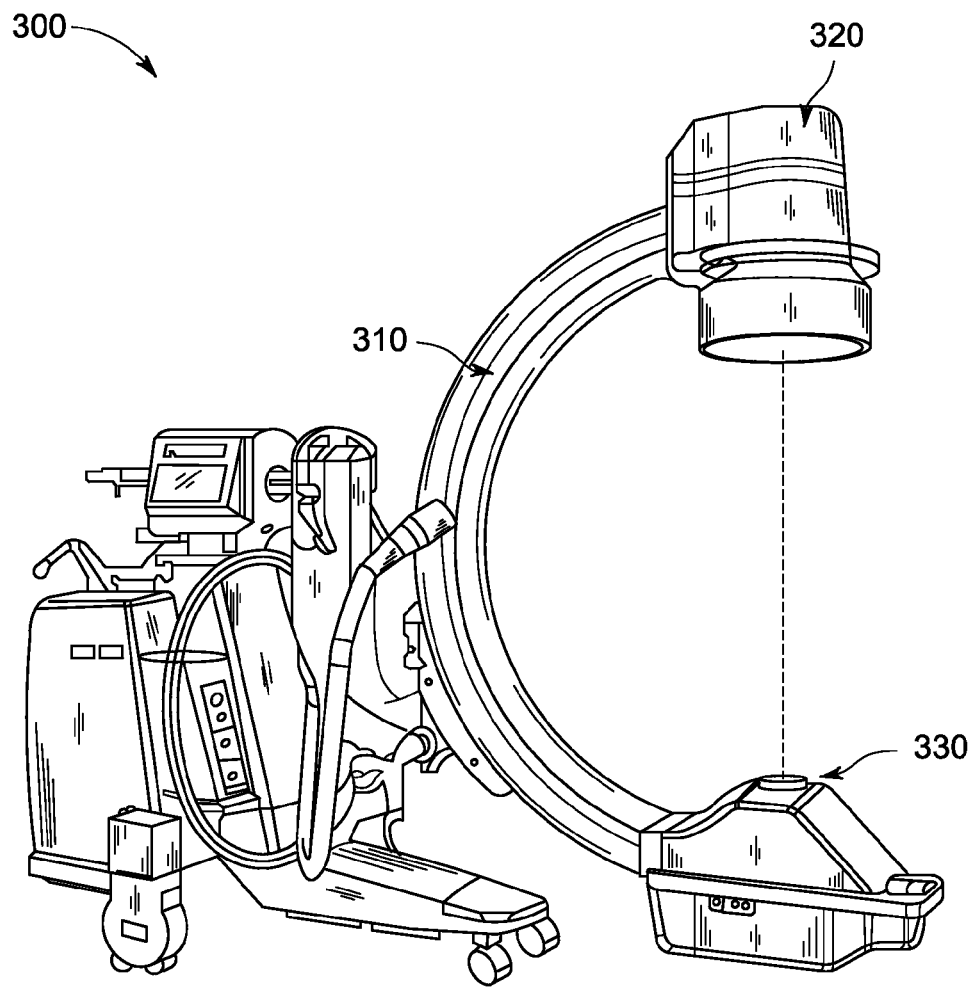
FIG. 5 is a perspective view of a mobile imaging system formed in accordance with various embodiments.

The imaging system 100 may be implemented as a non-mobile (as shown in FIG. 4) or mobile imaging system as shown in FIG. 5. For example, FIG. 5 illustrates a mobile imaging system 300 that may be used in accordance with one embodiment and configured as a mobile fluoroscopic imaging system. The mobile imaging system 300 may include some or all of the imaging system 100, 200 or a similar system. The mobile imaging system 300 includes a C-arm 310, an energy source 320 (e.g., an x-ray energy source), an image acquisition device 330 (e.g., a detector or camera) and a positioning surface (e.g., a patient positioning table, not shown). Optionally, the C-arm 310 may be, for example, an L-arm, an O-arm, a C-gantry, and/or other positioning element. Also, the imaging system 100 may be implemented as a stand-alone or wall mounted unit.

In operation, an object may be positioned on the positioning surface. Image data related to the object may be obtained at the image acquisition device 330 after energy from the energy source 320 has irradiated the object. Thus, fluoroscopic images may be acquired of patient or a region of interest of the patient.

Various embodiments provide multiple screen display portions or a multi-monitor (e.g., dual monitor) configuration wherein real-time or live fluoro images are displayed on a display monitor (or a portion thereof), referred to generally as the acquisition display, and user controls and stored images are displayed on another display monitor or a different portion of the same display monitor, referred to generally as the review display. One embodiment of user interfaces 400 and 500 are illustrated in FIGS. 6 and 7, respectively. In operation, during acquisition of fluoro exposures, fluoro sequences and the last image of the sequence (LIH) are displayed, such as in a sequential panel on the acquisition display to alert the user that system is storing all fluoro sequences. Thumbnail views of images also may be provided. A user may, during the exam, review the fluoro sequences, store all or part of fluoro sequences to a permanent save or store and/or select specific images in a sequence to store. These images may be the last image of the sequence or any image within the sequence. Images saved within a sequence may be enhanced or optimized as described in more detail above.

Images that have been selected may be transmitted to a DICOM PACS. Additionally, printing of images in various embodiments is performed using a defined area (storyboard) to separately identify and indicate saved images. Prior to closing an exam, in various embodiments, if no images or sequences have been saved to a permanent store memory, a user may be prompted and requested to confirm that none of the images or sequences are to be stored or to store one or more of the images or sequences.

In particular, FIG. 6 illustrates an image acquisition interface 400 and FIG. 7 illustrates a review interface 500, both of which may be selected by the user. It should be noted that the interfaces 400 and 500 may be provided as part of a dual-monitor display or on separate portions of the same display (e.g., side by side display). Moreover, the different areas or windows of each of the interfaces 400 and 500 may be modified and moved as desired or needed, such that the areas or windows are positioned and sized differently on the display.

The image acquisition interface 400 includes a real-time display portion 402 and a selected image potion 404. The real-time display portion 402 includes a live fluoro image window 406 displaying a current fluoro image that is acquired and a sequential image panel 408 that includes images 410 (e.g., thumbnail images) that are being added as a user is viewing the sequence of images. Additionally a spot selection element 412 (e.g., virtual displayed button) also may be provided that is selectable by a user, for example, with a mouse or trackball. Selection of the spot selection element 412 initiates an image enhancement process as described in more detail herein.

The selected image potion 404 includes a plurality of images 414 (or sequences of images), which may be displayed concurrently, such as in a single window or quad-window arrangement, with the latter being shown in FIG. 6. The images 414 are those images selected by a user to be maintained in memory, such as in the permanent store memory instead of in the persistent store memory. A control portion 416 also may be provided to display control options (e.g., protocol selection) in any suitable manner that may be selected by a user. Additionally, a status bar 418 may be displayed, which shows, for example, a current status or percentage of completion of a processing operation. The selected image potion 404 also includes a plurality of utility/application selection elements 420, which may be selectable by a user to initiate different utilities or applications, which may be displayed in different windows or on different interfaces.

The user interface 500 shown in FIG. 7 includes an image review portion 502, which replaces the selected image potion 404 on the display. It should be noted that like numeral represent like part or elements in the various Figures. The user interface 500 includes a viewer tools control portion 504 having a plurality of selection elements 506 that allows a user to select different operations to be performed in connection with selected images, for example, to add annotations to the images to be saved or further process the images for sending for printing or viewing with a DICOM PACS workstation.

The image review portion 502 also includes a current selected image window 507 displaying a current selected image that may be further processed using the viewer tools of the viewer tools control portion 504. Additionally, a selected image panel 508 includes images 510 (e.g., thumbnail images) that have been selected and which may be reviewed and processed. Additionally, a tool bar 512 may be provided that includes selectable elements to facilitate the processing and review of the selected images, which may include any suitable tools (e.g., image crop, image rotate, etc.).

Thus, various embodiments provide a persistent storing of fluoro images during image acquisition. The storing of the fluoro images is performed without user interaction, for example, user initiation of a record function during a fluoro mode.

Some embodiments of the present invention provide a machine-readable medium or media having instructions recorded thereon for a processor or computer to operate an imaging apparatus to perform one or more embodiments of the methods described herein. The medium or media may be any type of CD-ROM, DVD, floppy disk, hard disk, optical disk, flash RAM drive, or other type of computer-readable medium or a combination thereof.

The various embodiments and/or components, for example, the processors, or components and controllers therein, also may be implemented as part of one or more computers or processors. The computer or processor may include a computing device, an input device, a display unit and an interface, for example, for accessing the Internet. The computer or processor may include a microprocessor and/or a Graphics Processing Unit (GPU). The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for archiving x-ray fluoroscopic images, the method comprising:
   receiving fluoroscopic images from a fluoroscopic imaging system;
   storing all of the received fluoroscopic images during an entire image acquisition scan by the fluoroscopic imaging system to a persistent store memory, the received fluoroscopic images being displayed during the image acquisition scan; and
   storing at least some of the fluoroscopic images stored in the persistent store memory to a permanent store memory based on a received user selection input.

2. A method in accordance with claim 1 wherein storing all of the received fluoroscopic images is performed without user interaction or input.

3. A method in accordance with claim 1 wherein the fluoroscopic images are displayed as fluoroscopic sequences during image acquisition.

4. A method in accordance with claim 1 wherein the persistent store memory and the permanent store memory comprise a same memory portion.

5. A method in accordance with claim 1 wherein storing all of the received fluoroscopic images comprises storing the fluoroscopic images directly to a hard disk drive of the fluoroscopic imaging system.

6. A method in accordance with claim 1 further comprising a user interface for display of the fluoroscopic images and configured to allow review of the stored fluoroscopic images and to receive user inputs selecting fluoroscopic images for further processing or action.

7. A method in accordance with claim 1 further comprising receiving a user input selecting at least some of the fluoroscopic images stored in the persistent store memory for permanent storing after the image acquisition scan.

8. A method in accordance with claim 1 wherein the images comprise a plurality of image sequences with a last image hold (LIH).

9. A method in accordance with claim 1 wherein storing all of the received fluoroscopic images comprises storing all fluoroscopic images that are displayed.

10. A method in accordance with claim 1 wherein the fluoroscopic images form exposure sequences and further comprising discarding short exposure sequences based on at least one of a user preference, an exam type or a patient type.

11. A method in accordance with claim 1 wherein storing all of the received fluoroscopic images during the entire image acquisition scan comprises storing every fluoroscopic image received from the fluoroscopic imaging system throughout the entire image acquisition scan from start to finish, and deleting the stored images only after a predetermined period of time greater than the duration of the scan or in response to a user preference.

12. A method in accordance with claim 1 further comprising displaying, during or after the image acquisition scan, the fluoroscopic images stored in the persistent store memory for user review and selection of images for long term storage in the permanent store memory.

13. A method for archiving x-ray fluoroscopic images, the method comprising:
   storing on a persistent basis all of a plurality of fluoroscopic image sequences acquired during an entire imaging scan using a fluoroscopic imaging system, wherein the fluoroscopic image sequences are stored directly to a memory storage device of the fluoroscopic imaging system; and
   storing on a permanent basis at least some of the plurality of fluoroscopic image sequences previously stored on a persistent basis.

14. A method in accordance with claim 13 further comprising deleting the fluoroscopic image sequences that are not stored on a permanent basis.

15. A method in accordance with claim 13 further comprising receiving a user input selecting one or more of the fluoroscopic image sequences stored on a persistent basis to be stored on a permanent basis, wherein non-selected sequences are not stored on a permanent basis.

16. A method in accordance with claim 13 further comprising determining whether to store sequences below a time period based on one or more preferences.

17. An x-ray fluoroscopy imaging system comprising:
an x-ray generator configured to generate and emit low dose x-rays;
an x-ray detector configured to detect low dose x-rays emitted from the x-ray generator after passing through an object to generate low dose x-ray fluoroscopy data;
a persistent memory configured to store on a persistent basis all of the low dose x-ray fluoroscopy data from the x-ray detector acquired during an entire imaging scan;
a display configured to display fluoroscopic images generated from the low dose x-ray fluoroscopy data, wherein the fluoroscopic images are displayed during acquisition of the low dose x-ray fluoroscopy data; and
a permanent memory configured to store on a permanent basis select low dose x-ray fluoroscopy data previously stored in the persistent memory.

18. An x-ray fluoroscopy imaging system in accordance with claim 17 wherein all of the low dose x-ray fluoroscopy data acquired during an imaging scan is stored in the persistent memory without user interaction.

19. An x-ray fluoroscopy imaging system in accordance with claim 17 further comprising a user interface for selecting low dose x-ray fluoroscopy data for permanent storing corresponding to at least some of the displayed fluoroscopic images.

20. An x-ray fluoroscopy imaging system in accordance with claim 19 wherein the user interface is configured to allow, either during or after the imaging scan, user review and selection of fluoroscopic images generated from the low dose x-ray fluoroscopy data stored in the persistent memory for permanent storing or further processing.

21. An x-ray fluoroscopy imaging system in accordance with claim 17 further comprising a persistent fluoro module configured to automatically store the low dose x-ray fluoroscopy data directly to the memory, wherein the memory comprises a hard disk drive.

* * * * *